United States Patent

Southcott

[11] Patent Number: 5,026,871
[45] Date of Patent: Jun. 25, 1991

[54] OLIGOMERS USEFUL FOR MAKING CURED FIBRE REINFORCED COMPOSITES

[75] Inventor: Mark R. Southcott, Cambridge, England

[73] Assignee: Ciba-Geigy Corporation, Ardsley, N.Y.

[21] Appl. No.: 601,146

[22] Filed: Oct. 22, 1990

[30] Foreign Application Priority Data

Oct. 26, 1989 [GB] United Kingdom ............... 8924143

[51] Int. Cl.$^5$ .......................................... C07D 209/70
[52] U.S. Cl. .................................................. 548/435
[58] Field of Search ........................................ 548/435

Primary Examiner—Mary C. Lee
Assistant Examiner—Michael G. Ambrose
Attorney, Agent, or Firm—Harry Falber

[57] ABSTRACT

The invention provides a compound of the general formula I

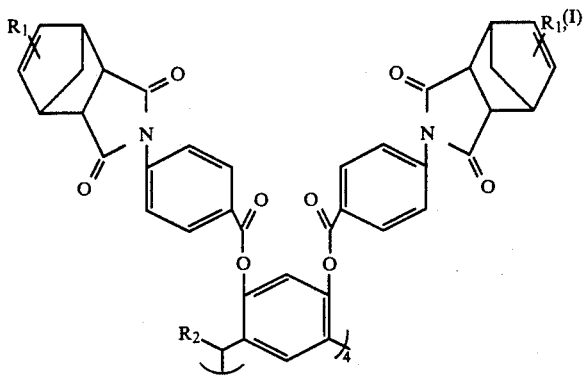

in which $R_1$ is hydrogen or methyl and $R_2$ is $C_1$-$C_{12}$alkyl, preferably methyl or ethyl.

2 Claims, No Drawings

NOVEL OLIGOMERS USEFUL FOR MAKING CURED FIBRE REINFORCED COMPOSITES

The present invention relates to novel curable oligomers containing imide groups and the use thereof.

Accordingly the invention provides oligomers of the general formula I

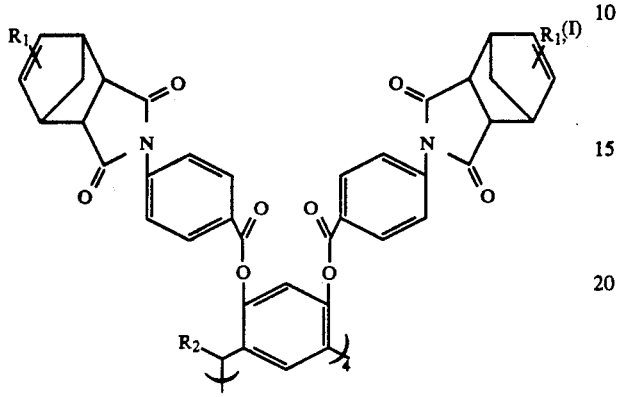

in which $R_1$ is hydrogen or methyl and $R_2$ is $C_1$-$C_{12}$ alkyl, preferably methyl or ethyl.

The compounds of formula I may be prepared by reacting a compound of general formula II

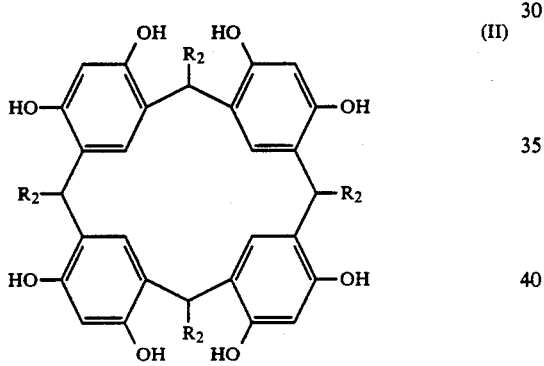

with a compound of the general formula III

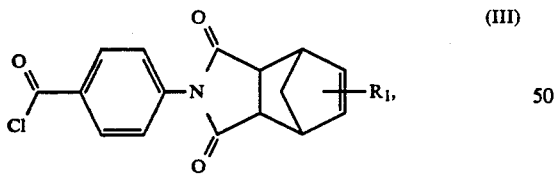

where $R_1$ and $R_2$ are as defined above, in the presence of an acid acceptor and under anhydrous conditions.

The reaction may be carried out in an inert organic solvent such as dimethylacetamide at temperatures of up to 200° C., but preferably at temperatures from 20° to 50° C. Suitable acid acceptors include amines such as methylamine and triethylamine.

The compounds of general formula II are known (see Cram et al., J. Org. Chem. 54, 1305 (1985)).

The compound of general formula III where $R_1$ is hydrogen is known (see Hahn et al., Acta. Pol. Pharm. 44(2), 159–66(1987)). The corresponding compound where $R_1$ is methyl is new but can be made by the same process as that where $R_1$ is hydrogen.

Thus the compounds of general formula III may be prepared by converting the benzoic acid derivative of the general formula IV

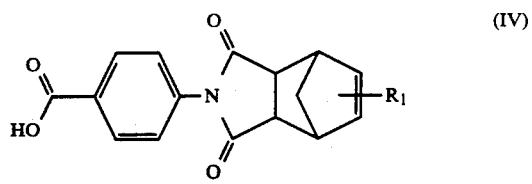

into the acid chloride by methods known per se for making acid chlorides. For example the compound of general formula IV may be reacted with a chlorinating agent such as thionyl chloride at elevated temperature.

The compounds of formula IV are known (see Kleinrok et al., Acta. Pol. Pharm. 31(5), 701 (1974) and B. S. Rao, J. Polym. Sci., Part C: Polym. Lett. 27(4), 133–140 (1989)). These compounds may be prepared by reacting 4-aminobenzoic acid with the dicarboxylic anhydride of the formula V

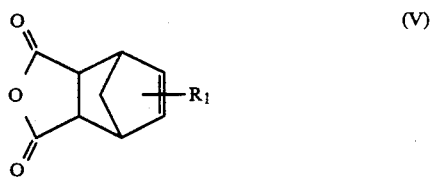

in an organic solvent at elevated temperatures.

The oligomers of the invention are useful for making cured fibre reinforced composites which have high strength, high glass transition temperatures, and unlike most polyimides with high glass transition temperatures, the cure does not result in the production of volatile components. As a result the composites do not have voids.

The oligomers of the invention are soluble in common organic solvents such as alcohol, e.g., methanol, ethanol, isopropanol, 2-butoxyethanol, and diethyleneglycol monobutyl ether; ketones, e.g., acetone, methyl ethyl ketone and methyl isobutyl ketone; and hydrocarbons, e.g., toluene and xylene. This allows facile coating onto fibres such as glass, carbon, boron, stainless steel, tungsten, aluminium, silicon, asbestos or an aromatic polyamide, but preferably carbon fibres.

The fibres may be in the form of woven or non-woven cloth. Thus the compounds of the invention may be used to produce prepregs wherein one or more layers of cloth incorporating fibres coated with the oligomers can be moulded using conventional moulding techniques and the oligomers cured at the elevated temperatures. The heating may be carried out in stages, first at 170° to 230° C.

The invention is illustrated by the following examples.

Preparation of
4-(1,3,3a,4,7,7a-hexahydro-1,3-dioxo-4,7-methano-2H-isoindol-2-yl)benzoic acid To 4-aminobenzoic acid (800 g, 5.83 mol) is added dimethylacetamide (2.5 l), toluene (1 l), and slowly with stirring bicyclo[2.2.1]hept-5-ene-2,3-dicarboxylic anhydride (956 g, 5.83 mol). After the addition the mixture is stirred for 1 hour, raised to 140° C. with removal of water (100 ml) azeotropically and then raised to 165° C.

to remove the toluene. The mixture is cooled and the product precipitated into water (3 l). Filtration, washing with water, drying in an oven at 80° C. and recrystallisation from ethanol yields a white crystalline solid (1.56 kg, 94%). M.p.: 224°–228° C.

Preparation of 4-(1,3,3a,4,7,7a-hexahydro-1,3-dioxo-5(6)-methyl-4,7-methano-2H-isoindol-2-yl)benzoic acid The title acid is isolated, after recrystallisation from ethanol, in 27% yield (80.5 g) from the reaction procedure described for the preparation of 4-(1,3,3a,4,7,7a-hexahydro-1,3-dioxo-4,7-methano-2H-isoindol-2-yl)benzoic acid, replacing bicyclo[2.2.1]hept-5-ene-2,3-dicarboxylic anhydride with bicyclo[2.2.1]hept-5-ene-5(6)-methyl-2,3-dicarboxylic anhydride (1041 g, 5.83 mol). M.p.: 231°–233° C.

Analysis: Found: C 68.4%; H 5.0%; N 4.8%. $C_{17}H_{16}NO_4$, Requires: C 68.4%; H 5.0%; N 4.8%.

IR(KBr disc): 2400–3500 cm$^{-1}$ (broad OH); 1780 and 1710 cm$^{-1}$ (C=O imide); 1680 cm$^{-1}$ (C=O acid).

NMR (acetone-d$_6$): 1.55(s-2H); 1.85(d-3H); 2.5–4.0(broad s-1H); 2.9–3.2(m-4H); 5.9(s-1H); 7.35–8.2(q-4H).

Preparation of 4-(1,3,3a,4,7,7a-hexahydro-1,3-dioxo-4,7-methano-2H-isoindol-2-yl)benzoyl chloride To 4-(1,3,3a,4,7,7a-hexahydro-1,3-dioxo-4,7-methano-2H-isoindol-2-yl)benzoic acid (1.56 kg, 5.48 mol), under nitrogen, is added, slowly thionyl chloride (2 l). After the addition the mixture is stirred for 1 hour after which the temperature is raised over a 1 hour period to 70° C. and stirred for a further hour. Half the thionyl chloride is removed under vacuum and a solution of CCl$_4$, CH$_3$CHCl$_2$ and hexane 1:1:1 (2 l) is added. The resultant precipitate is filtered, washed with more of the solvent mixture and dried in a dessiccator over NaOH overnight giving 91% of the title acid chloride (1.503 kg). M.p.: >300° C.

Analysis: Found: C 63.0%; H 4.1%; N 4.7%. $C_{16}H_{12}ClNO_3$, Requires: C 63.6%; H 3.9%; N 4.6%.

IR(KBr disc): 1760 and 1740 cm$^{-1}$ (C=O imide); 1700 cm$^{-1}$ (C=O acid chloride).

NMR (acetone-d$_6$): 1.7(d-2H); 3.4–3.6(m-4H); 6.2(d-2H); 7.4–8.2(q-4H).

Preparation of 4-(1,3,3a,4,7,7a-hexahydro-1,3-dioxo-5(6)-methyl-4,7-methano-2H-isoindol-2-yl)benzoyl chloride The title acid chloride isolated in 85% yield (1.469 kg) following the reaction procedure used to prepare 4-(1,3,3a,4,7,7a-hexahydro-1,3-dioxo-4,7-methano-2H-isoindol-2-yl)benzoyl chloride, replacing 4-(1,3,3a,4,7,7a-hexahydro-1,3-dioxo-4,7-methano-2H-isoindol-2-yl)benzoic acid with 4-(1,3,3a,4,7,7a-hexahydro-1,3-dioxo-5(6)-methyl-4,7-methano-2H-isoindol-2-yl)benzoic acid (1.728 kg). M.p.: >300° C.

Analysis: Found: C 64.5%; H 4.6%; N 4.1%. $C_{17}H_{14}ClNO_3$, Requires: C 64.6%; H 4.4%; N 4.4%.

IR(KBr disc): 1780 and 1740 cm$^{-1}$ (C=O imide); 1710 cm$^{-1}$ (C=O acid chloride).

NMR (acetone-d$_6$): 1.5(s-3H); 1.8(s-2H); 2.8–3.2(m-4H); 5.9(d-2H); 7.5–8.2(q-4H).

EXAMPLE 1

Preparation of 2,8,14,20-tetramethylpentacyclo-[19.3.1.1$^{3,7}$.1$^{9,13}$.1$^{15,16}$]octacosa-1(25)3,5,7(28),9,1-1,13-(27),15,17,19(26),21,23-dodecaene-4,6,10,12,16,18,22,24-octa-[4-(1,3,3a,4,7,7a-hexahydro-1,3-dioxo-4,7-methano-2H-isoindol-2-yl)benzoate]

To a solution of 2,8,14,20-tetramethylpentacyclo[19.3.1.-1$^{3,7}$.1$^{9,13}$.1$^{15,19}$]octacosa-1(25),3,5,7(28),9,11,13(27),15,-17,19(26),21,23-dodecaene-4,6,10,12,16,18,22,24-octol (169.5 g, 0.3115 mol) in dimethylacetamide (0.5 l) that has been dried over molecular sieves, is added, at 50° C., triethylamine (251.7 g, 2.49 mol) and slowly with stirring 4-(1,3,3a,4,7,7a-hexahydro-1,3-dioxo-4,7-methano-2H-isoindol-2-yl)benzoyl chloride (751.5 g, 2.49 mol). After the addition the mixture is stirred for 1 hour and then filtered. The product is precipitated onto water (2 l), filtered, washed with water and dried in an oven at 100° C. overnight. The title octaester is isolated as a cream coloured powder in 99% yield (821.5 g).

Analysis: Found: C 70.5%; H 5.1%; N 4.8%. $C_{160}H_{120}N_8O_{32}$.4 H$_2$O, Requires: C 70.2%; H 4.7%; N 4.1%.

IR (KBr disc): 1780 and 1740 cm$^{-1}$ (C=O imide); 1715 cm$^{-1}$ (C=O ester).

NMR (CDCl$_3$): 1.3–2.0(m-28H); 2.9–3.1(m-4H); 3.4–3.6(d-32H); 6.25(s-16H); 6.8–8.4(m-40H).

EXAMPLE 2

Preparation of 2,8,14,20-tetraethylpentacyclo-[19.3.1.1$^{3,7}$.1$^{9,13}$.1$^{15,19}$]octacosa-1(25)3,5,7(28),9,11,13-(27),15,17,19(26),21,23-dodecaene-4,6,10,12,16,18,22,24-octa-[4-(1,3,3a,4,7,7a-hexahydro-1,3-dioxo-4,7-methano-2H-isoindol-2-yl)benzoate]

The title octaester is isolated in 64% yield (542.2 g) following the reaction procedure described in Example 1 replacing 2,8,14,20-tetramethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol with 2,8,14,20-tetraethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol (186.9 g, 0.3115 mol).

Analysis: Found: C 70.4%; H 5.6%; N 4.1%. $C_{164}H_{126}N_8O_{32}$.4 H$_2$O, Requires: C 70.5%; H 4.7%; N 4.0%.

IR (KBr disc): 1770 and 1740 cm$^{-1}$ (C=O imide); 1700 cm$^{-1}$ (C=O ester).

NMR (acetone-d$_6$): 0.8–1.2(m-12H); 1.6(s-16H); 2.0(m-8H); 2.8–3.0(m-4H); 3.4–3.55(m-32H); 6.25(s-16H); 7.2–8.2(m-40H).

EXAMPLE 3

Preparation of 2,8,14,20-tetramethylpentacyclo-[19.3.1.1$^{3,7}$.1$^{9,13}$.1$^{15,19}$]octacosa-1(25)3,5,7(28),9,11,13(27),15,17,19(26),21,23-dodecaene-4,6,10,12,16,18,22,24-octa-[4-(1,3,3a,4,7,7a-hexahydro-1,3-dioxo-5(6)-methyl-4,7-methano-2H-isoindol-2-yl)benzoate]

The title ester is isolated in 99% yield (856.1 g) following the reaction procedure described in Example 1 replacing 4-(1,3,3a,4,7,7a-hexahydro-1,3-dioxo-4,7-methano-2H-isoindol-2-yl)benzoyl chloride with 4-

(1,3,3a,4,7,7a-hexahydro-1,3-dioxo-5(6)-methyl-4,7-methano-2H-isoindol-2-yl)benzoyl chloride (785.5 g, 2.49 mol).

Analysis: Found: C 70.6%; H 5.0%; N 3.4%. $C_{168}H_{132}N_8O_{32}.4\ H_2O$, Requires: C 70.8%; H 4.9%; N 3.9%.

IR (KBr disc): 1770 and 1740 cm$^{-1}$ (C=O imide); 1700 cm$^{-1}$ (C=O ester).

NMR (acetone-$d_6$): 1.5-2.2(m-52H); 2.9-3.2(m-36H); 5.9(s-8H); 7.1-8.2(m-40H).

EXAMPLE 4

Preparation of 2,8,14,20-tetraethylpentacyclo-[19.3.1.1$^{3,7}$.1$^{9,1}$ 3.1$^{15,19}$]octacosa-1(25)3,5,7(28),9,11,13-(27),15,17,19 (26),21,23-dodecaene-4,6,10,12,16,18,22,24-octa-[4-(1,3,3a,4,7,7a-hexahydro-1,3-dioxo-5(6)-methyl-4,7-methano-2H-isoindol-2-yl)benzoate]

The title octaester is isolated in 89% yield (784.5 g) following the reaction procedure described in Example 1 replacing 2,8,14,20-tetramethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol with 2,8,14,20-tetraethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol (186.9 g, 0.3115 mol) and 4-(1,3,3a,-4,7,7a-hexahydro-1,3-dioxo-4,7-methano-2H-isoindol-2-yl)-benzoyl chloride with 4-(1,3,3a,4,7,7a-hexahydro-1,3-dioxo-5(6)-methyl-4,7-methano-2H-isoindol-2-yl)benzoyl chloride (785.5 g, 2.49 mol).

Analysis: Found: C 71.0%; H 5.2%; N 3.7%. $C_{172}H_{140}N_8O_{32}.4\ H_2O$, Requires: C 71.2%; H 5.1%; N 3.8%.

IR (KBr disc): 1770 and 1740 cm$^{-1}$ (C=O imide); 1700 cm$^{-1}$ (C=O ester).

NMR (acetone-$d_6$): 0.7-1.2(m-12H); 1.55(s-16H); 1.85(s-24H); 1.9-2.1(m-8H); 2.7-3.3(m-36H); 5.9(s-8H); 7.4-8.2(m-40H).

Cure and Strength Testing of the Octaesters of Examples 1-4

The octaester (50 g) was dissolved in CH$_2$Cl$_2$ (100 ml) and coated onto carbon fibre (50 g; G814-plain weave). The prepreg was dried in an oven at 80° C. for 30 minutes and then cut into 16 20×10 cm inch sections, which were layed warp-to-warp/weft-to-weft. The laminate was cured in a press-clave using the cure-cycle shown and post-cured at 300° C. overnight. The glass transition temperature (Tg's) and Tan were obtained by Dynamic Mechanical Thermal Analysis (DMTA) (10 Hz; strain×1; dual cant).

Cure-cycle: Temperature: Raise to 170°-230° C. at 1-5 °C./min; hold
Parameters: for 1-2 hours; raise to 270°-330° C. at 1-3 °C./min; hold for 2-3 hours. Cool to R/T slowly.
Vacuum: Full vacuum throughout cure.
Pressure: 0.69 MN/m$^2$ (100 p.s.i.) on at 270°-330° C. until end of cure.

| Octaester of Example | Tg/°C. | Tan δ/°C. |
|---|---|---|
| 1 | 400 | 435 |
| 2 | 400 | 430 |
| 3 | 400 | 440 |
| 4 | 400 | 430 |

Fracture testing of the laminate prepared using the octaester of Example 1 using an Instron IX; double cant beam, gave the following results:
$G_{Ic}$: 14.5 MN/m$^2$
$G_{IIc}$: 27.4 MN/m$^2$

EXAMPLE 5

Preparation of 2,8,14,20-tetrapentylpentacyclo-[19.3.1.1$^{3,7}$.1$^{9,1}$ 3.1$^{15,19}$]octacosa-1(25)3,5,7(28),9,1-1,13-(27),15,17,19(26),21,23-dodecaene-4,6,10,12,16,18,22,24-octa-[4-(1,3,3a,4,7,7a-hexahydro-1,3-dioxo-4,7-methano-2H-isoindol-2-yl)benzoate]

The title octaester is isolated in 66% yield (24.6 g) following the reaction procedure described in Example 1 replacing 2,8,14,20-tetramethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol with 2,8,14,20-tetrapentylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol (10.0 g, 0.013 mol) in 30 ml N-methyl-2-pyrrolidone (NMP) using the same mole proportions of the other reagents.

Analysis: Found: C 70.59%; H 5.39%; N 4.06%. $C_{176}H_{152}N_8O_{32}.4\ H_2O.2\ NMP$, Requires: C 70.96%; H 5.78%; N 4.36%.

IR (KBr disc): 1780 (C=O imide); 1710 cm$^{-1}$ (C=O ester).

NMR (CDCl$_3$): 0.6-2.5(63H); 3.3-3.6(34H); 4.2-4.3(1H); 6.0-6.7(19H); 6.8-7.4(22H); 7.8-8.3(15H); NMP peaks at 2.0, 2.8 and 3.4.

EXAMPLE 6

Preparation of 2,8,14,20-tetraheptylpentacyclo-[19.3.1.1$^{3,7}$.1$^{9,1}$ 3.1$^{15,19}$]octacosa-1(25)3,5,7(28),9,1-1,13-(27),15,17,19(26),21,23-dodecaene-4,6,10,12,16,18,22,24-octa-[4-(1,3,3a,4,7,7a-hexahydro-1,3-dioxo-4,7-methano-2H-isoindol-2-yl)benzoate]

The title octaester is isolated in 75% yield (25.6 g) following the reaction procedure described in Example 1 replacing 2,8,14,20-tetramethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol with 2,8,14,20-tetraheptylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol (10.0 g, 0.0114 mol) in 30 ml N-methyl-2-pyrrolidone (NMP) using the same mole proportions of the other reagents.

Analysis: Found: C 71.8%; H 5.84%; N 3.68%. $C_{184}H_{168}N_8O_{32}.4\ H_2O.2\ NMP$, Requires: C 71.4%; H 6.07%; N 4.21%.

IR (KBr disc): 1770-1780 cm$^{-1}$ (C=O imide); 1710 cm$^{-1}$ (C=O ester).

NMR (CDCl$_3$): 0.7-2.5 (92H); 3.3-3.7(35H); 4.4-4.5(1H); 6.1-6.7(19H); 6.8-7.5(21H); 7.7-8.4(16H); NMP peaks at 2.2, 2.7 and 3.3, H$_2$O peaks at 2.7-3.1.

EXAMPLE 7

Preparation of
2,8,14,20-tetraundecylpentacyclo-[19.3.1.1$^{3,7}$.1$^{9,13}$.1$^{15,19}$]octacosa-1(25)3,5,7(28),9,1-1,13-(27),15,17,19(26),21,23-dodecaene-4,6,10,12,16,18,22,24-octa-[4-(1,3,3a,4,7,7a-hexahydro-1,3-dioxo-4,7-methano-2H-isoindol-2-yl)benzoate]

The title octaester is isolated in 82.1% yield (24.1 g) following the reaction procedure described in Example 1 replacing 2,8,14,20-tetramethylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol with 2,8,14,20-tetraundecylpentacyclo[19.3.1.1$^{3,7}$.1$^{9,13}$.1$^{15,19}$]octacosa-1(25),3,5,7(28),9,11,13(27),15,17,19(26),21,23-dodecaene-4,6,10,12,16,18,22,24-octol (10.0 g, 0.0091 mol) in 30 ml N-methyl-2-pyrrolidone (NMP) using the same mole proportions of the other reagents.

Analysis: Found: C 72.58%; H 6.56%; N 3.32%. $C_{200}H_{200}N_8O_{32}.4\ H_2O.2$ NMP, Requires: C 72.14%; H 6.46%; N 4.01%.

IR (KBr disc): 1780–1790 cm$^{-1}$ (C=O imide); 1715 cm$^{-1}$ (C=O ester).

NMR (CDCl$_3$): 0.8–2.2(134H); 3.4–3.7(40H); 4.2–4.4(1H); 6.1–6.5(19H); 6.9–7.5(20H); 7.7–8.3(17H); NMP peaks at 2.1, 2.7 and 3.3, H$_2$O peaks at 2.8–3.0.

Cure and Testing of the Octaesters of Examples 5-7

The octaester powder is cured in an open mould at atmospheric pressure.

Cure-cycle: Temperature: 200° C. for 1.5 h, raise to 250° C. for 1 h;
Parameters: raised to 300° C. and cure for about 18 h.

The glass transition temperature as measured by fall off in log E is obtained by Dynamic Mechanical Thermal Analysis (DMTA) (10 Hz; strain×1; dual cant).

| Octaester of Example | Tg/°C. |
|---|---|
| 5 | 375 |
| 6 | 400 |
| 7 | 390 |

We claim:
1. A compound of the general formula I

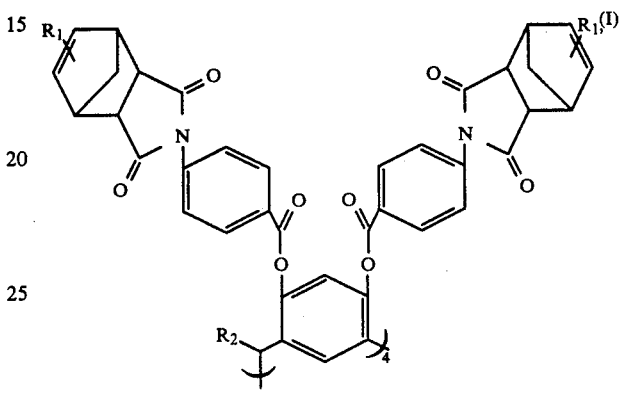

in which R$_1$ is hydrogen or methyl and R$_2$ is C$_1$–C$_{12}$ alkyl.

2. A compound according to claim 1 in which R$_2$ is methyl or ethyl.

* * * * *